(12) United States Patent
Preaudat et al.

(10) Patent No.: US 7,838,211 B2
(45) Date of Patent: Nov. 23, 2010

(54) METHOD FOR DETERMINING ENDOGLYCOSIDASE ENZYME ACTIVITY

(75) Inventors: Marc Preaudat, Connaux (FR); Chikashi Tokuda, Chiba (JP); Laurence Jacquemart, Uzes (FR)

(73) Assignee: Cis Bio International, Saclay (FR)

( * ) Notice: Subject to any disclaimer, the term of this patent is extended or adjusted under 35 U.S.C. 154(b) by 1032 days.

(21) Appl. No.: 10/522,909

(22) PCT Filed: Jul. 31, 2003

(86) PCT No.: PCT/EP03/09315

§ 371 (c)(1),
(2), (4) Date: Oct. 5, 2005

(87) PCT Pub. No.: WO2004/013348

PCT Pub. Date: Feb. 12, 2004

(65) Prior Publication Data

US 2006/0127945 A1 Jun. 15, 2006

(30) Foreign Application Priority Data

Aug. 1, 2002 (FR) .................................. 02 09836

(51) Int. Cl.
*C12Q 1/00* (2006.01)

(52) U.S. Cl. ......................................................... 435/4
(58) Field of Classification Search ....................... None
See application file for complete search history.

(56) References Cited

U.S. PATENT DOCUMENTS 4,859,581 A 8/1989 Irimura et al.
6,190,875 B1 2/2001 Ayal-Hershkovitz et al.

FOREIGN PATENT DOCUMENTS

WO WO 0077241 12/2000

OTHER PUBLICATIONS

Bazin et al. Spectrochimica Acta Part A 57(2001):2197-2211.*

* cited by examiner

*Primary Examiner*—Karen Cochrane Carlson
*Assistant Examiner*—Bin Shen
(74) *Attorney, Agent, or Firm*—Millen, White, Zelano, Branigan, P.C.

(57) ABSTRACT

The invention relates to a method for determining endoglycosidase enzyme activity, and in particular of the heparanase type, in a sample, and also to a method for detecting a compound capable of modulating the activity of an endoglycosidase, and in particular of an endoglycosidase having activity of the heparanase type, by measuring a signal resulting from a close proximity transfer between two compounds attached to a substrate for the enzyme.

10 Claims, 4 Drawing Sheets

METHOD FOR DETERMINING ENDOGLYCOSIDASE ENZYME ACTIVITY

FIELD AND STATE OF THE ART

The present invention relates to a method for determining endoglycosidase enzyme activity, and in particular of the heparanase type, in a sample, and also to a method for detecting a compound capable of modulating the activity of an endoglycosidase, and in particular of an endoglycosidase having activity of the heparanase type.

Endoglycosidases are enzymes capable of catalyzing cleavage reactions within glycosidic chains.

Heparanase is an enzyme capable of cleaving polymers comprising glycosaminoglycan units, such as, for example, heparan sulfate glycosaminoglycans (HSGAGs).

A major process of tissue invasion by cancerous cells of blood line tumors involves their passage across the blood vessel endothelium and then the degradation of the underlying basal laminar and of the extracellular matrix by a set of proteases and glycosidases.

The basal laminar and the underlying connective tissue are composed of a complex network of fibronectin, laminin, type IV collagen and vitronectin, each one interacting with the heparan sulfate (HS) side chains of the proteoglycans embedded in the extracellular matrix.

HS cleavage by endoglycosidases, for example enzymes having activity of the heparanase type, produced by the invasive cells can consequently contribute to degradation of the extracellular matrix and of the basal laminar and thus facilitate cell migration.

It has been shown that heparanase activity is linked to the metastatic potential of murine and human melanoma cell lines. In particular, the metastatic potential of human and murine fibrosarcoma and melanoma cell lines is related to the heparanase activity produced by these lines. Moreover, heparanase activity has been reported in several tissue and cell types, in particular rat liver, human placenta, human platelets, fibroblasts in culture, human neutrophiles, activated rat T lymphocytes, murine B lymphocytes and human monocytes, and in human umbilical vein endothelial cells.

Heparan sulfate proteoglycans (HSPGs) are made up of a protein component embedded in cell membranes, substituted with HS chains. These chains generally consist of sulfated disaccharide units (predominantly of N-sulfated glucosamine linked to an alpha-L-iduronic acid residue) separated by non-sulfated or relatively non-sulfated regions (predominantly disaccharide units of N-acetylated glucosamine linked to a unit of beta-D-glucuronic acid). HSs can exhibit great variety, due to the variable number of disaccharide units and to their sequence, which can differ from one chain to the other.

Insofar as the cleavage of the HSs appears to be essential to migration of metastatic cells across basal membranes, heparanase activity inhibitors constitute a new class of compounds which are potentially of use as anti-metastatic or anti-inflammatory medicinal products.

Several groups have developed assays for heparanase activity, in particular with the aim of isolating novel compounds which might be used as medicinal products.

Most of the methods developed for assaying heparanase activity are based on radiolabeling a heparanase substrate and analyzing the fragments generated after incubation with a sample containing this enzyme.

Application WO 00/77241 reports, in its introduction section, that radioactive atoms or groups ($^{35}$S, 3H) can be incorporated by HSGAGs by culturing cells in the presence of these radioelements. The radiolabeled HSGAG is then used as a substrate. It is also possible to label the HSGAG with $^3$H or $^{125}$I. The heparanase activity is determined by measuring a decrease in the radioactivity or a reduction in the molecular weight of the labeled molecules. In the latter case, the substrate is analyzed by electrophoresis or by chromatography.

These techniques have the usual drawbacks associated with the use of radioelements, in particular in terms of radioprotection; they are qualitative, make it possible to quantify the enzyme activity measured only with difficulty, and are not suitable for high throughput screening.

Application WO 00/77241 discloses a method for assaying heparanase activity based on the detection of HSGAG fragments cleaved by the enzyme present in the test sample. The HSGAG substrate is attached, firstly, to a solid support by means of a binding motif and, secondly, to a cell regulator capable of binding to the HSGAG (for example a growth factor). After having been brought into contact with the test sample, the cleaved fragments are immobilized by specific binding with a second solid support. The fragments thus separated can be detected, for example, using a labeled antibody specific for the binding group or for the growth factor, by colorimetry or fluorescence techniques. The signal measured is representative of the heparanase activity in the sample and directly reflects the biological activity of generation of growth factor/HSGAG complexes produced in physiological or pathological states. The drawback of this technique lies in the use of a solid support which can lead to problems of nonspecific adsorption, which increases the laboriousness and the costs of the assay, and also in the separation step which can be tedious in high throughput screening processes.

Application WO 00/03306 describes a glycosidase activity assay, and in particular a method for screening anticancer or anti-inflammatory agents. The method is based on studying the effect of a test agent on heparanase activity in the presence of a substrate of the HS type. The heparanase activity is determined by separating the fragments of cleaved substrate by column chromatography or by electrophoresis, with a calorimetric assay, in particular a colorimetric assay for detecting the reducing sugars formed during substrate cleavage.

In that application, the substrate is coupled to Sepharose® beads and a centrifugation step is necessary to separate the soluble cleaved fragments and to identify them by a colorimetric method (carbazole or dimethylmethylene blue).

U.S. Pat. No. 6,207,402 describes a method for detecting heparanase enzyme activity, comprising steps of separation and of detection of the products of degradation of a substrate for this enzyme.

Hydrolytic enzyme assays based on detecting fluorescence emitted by energy transfer have been described (caspase 3, herpes simplex virus protease, HIV protease), but, in all cases, the substrate was a protein or peptide substrate. Such substrates can be readily functionalized, which is not the case of substrates for endoglycosidases, such as heparanase or heparitinase. This is in particular due to the fact that HSs are produced by a set of complex biochemical processes and are therefore difficult to produce by chemical synthesis, and also to the very great diversity of heparan sulfates.

Combinatorial chemistry has produced libraries of compounds consisting of several hundreds of thousands of products. In order to test the advantage of these molecules within a reasonable amount of time and at reasonable cost, it is necessary to use simple, rapid, reliable models which can be readily automated. The techniques previously developed for assaying heparanase activity are relatively unsuitable for such a use, in particular in the context of the high throughput screening of molecule libraries.

The technical problem to be solved therefore consists in developing a technique which satisfies these criteria, in particular an assay for heparanase activity which is suitable for intensive use, which can be miniaturized and which is sensitive. The present invention provides such an assay.

DETAILED DESCRIPTION OF THE INVENTION

A subject of the present invention is the assaying of endoglycosidase activity based on measuring a signal resulting from a close proximity transfer between two compounds attached to the enzyme substrate, and therefore not requiring any step of separation of the fragments derived from the enzyme activity.

The close proximity transfer can be an energy transfer (FRET phenomenon, HTRF® technology, CIS bio international), a photon transfer, a singlet oxygen transfer (Alphascreen® technology, PerkinElmer, see, for example, Beaduet et al., Genome Res., 2001 Apr. 11 (4), 600-8), or an electron transfer (SPA technology, Amersham Biosciences, see, for example, Udenfriend et al., Anal. Biochem., 1987, Mar., 161 (2), 494-500).

The invention relates in particular to an assay for endoglycosidase activity based on homogeneous time-resolved measurement of fluorescence resulting from an energy transfer between a donor fluorescent compound and an acceptor fluorescent compound, which are attached to the substrate. Preferably, this endoglycosidase has activity of the heparanase type.

The FRET (fluorescence resonance energy transfer) phenomenon allows homogeneous time-resolved measurement of fluorescence. The use of this technique with rare earth cryptates or chelates, developed in particular by G. Mathis et al. (see in particular "Homogeneous time resolved fluorescence energy transfer using rare earth cryptates as a tool for probing molecular interactions in biology", *Spectrochimica Acta Part A* 57 (2001) 2197-2211) has many advantages which have already allowed several applications in the field of in vitro diagnosis and in that of high throughput screening in the pharmaceutical industry.

This technique, also referred to as HTRF® (Homogenous Time Resolved Fluorescence) uses a first donor fluorescent compound and a second acceptor fluorescent compound. In the method according to the invention, these compounds are directly or indirectly coupled to a substrate for an enzyme having endoglycosidase activity, in particular activity of the heparanase type.

After light excitation of the medium containing the substrate, an energy transfer takes place between the donor compound and the acceptor compound, resulting in an emission of light by the acceptor compound, which can be measured using a fluorimeter. In the presence of an enzyme having endoglycosidase activity, in particular activity of the heparanase type, the substrate is cleaved and, due to the distancing of the donor and acceptor compounds, the energy transfer will no longer take place, which will result in a decrease in the signal emitted by the acceptor compound.

In the presence of a compound which inhibits or activates endoglycosidase activity, in particular activity of the heparanase type, the signal measured will be modified compared to the signal measured in the absence of inhibitor or of activator.

Several technical obstacles have had to be taken into consideration in developing the methods according to the invention.

The distance between the first and second fluorescent compound constitutes a critical aspect in an assay using the FRET phenomenon. In particular, the energy transfer is inversely proportional to the distance between the donor and the acceptor raised to the power of 6. This aspect must be taken into account in labeling the substrate used in the assay according to the invention: the distance separating the first and second fluorescent compound must both allow the energy transfer to take place and allow the cleavage of the substrate to effectively bring about a distancing of the two fluorescent compounds.

Consequently, the amounts of each of the donor and acceptor fluorescent compounds must be optimized: if the substrate comprises too great a number of fluorescent compounds, the signal observed will not vary significantly during the cleavage by an enzyme having endoglycosidase activity, in particular activity of the heparanase type. In the opposite case, if too few fluorescent compounds are used, the energy transfer will not take place, which will result in a lack of signal. The inventors have thus optimized the proportions of donor and acceptor fluorescent compounds to be used to functionalize the substrate. These proportions correspond to the initial molar ratio (Rmi) and to the final molar ratio (Rmf) for each fluorophore. The Rmi corresponds to the proportion of fluorophore relative to the substrate during the labeling reaction. If the fluorophore is indirectly coupled to the substrate, via a ligand/receptor pair, the Rmi will correspond to the proportion of ligand to the amount of substrate. The Rmf is calculated in the same way, but after the labeling reaction: it therefore corresponds to the number of molecules of fluorophore or of ligand attached to the substrate.

Other parameters had to be taken into consideration during the production of the substrate which can be used in the methods according to the invention.

The pH of the reaction medium plays an important role during the labeling reaction, in particular if the amine or carboxyl groups of the heparan sulfate are used in the coupling of the donor fluorescent compound, of the acceptor fluorescent compound, or of a member of a ligand/receptor pair. In fact, the pH determines the reactivity of the amine or carboxyl functions used in the functionalization of the substrate. The inventors have thus determined that the optimum pH for producing a substrate which can be used in the methods according to the invention is within a range of 7.5 to 9, and is preferably equal to 8.3, when the free amines of the HS are used, and within a range of 5 to 7, preferably equal to 6, when free carboxyl functions are used.

In order to develop an assay for endoglycosidase activity, and in particular enzyme activity of the heparanase type, based on the FRET phenomena, the inventors had to overcome a certain number of technical difficulties specifically encountered when assaying these enzymes, which are not apparent in assays for protein substrates or for other enzyme activities:

1/ In the assays for enzyme activities based on the FRET technique of the prior art, the enzyme cleavage sites are clearly characterized whereas uncertainties remain regarding HS: it is, consequently, very difficult to functionalize the substrate on both sides of the cleavage site.

2/ HSs exhibit very great heterogeneity both with regard to the sequence of the glycosidic units and the length of the chains: a chemically localized functionalization is therefore difficult to obtain since the structure of the HSs varies from one molecule to another.

3/ Protein-HS interactions are much less stable than protein-protein interactions: the direct or indirect attachment of the donor and acceptor compounds can all the more readily disturb the endoglycosidase/HS interaction.

The invention relates, firstly, to a method for determining endoglycosidase enzyme activity in a sample, comprising the following steps:
  i. bringing a substrate which can be cleaved by an endoglycosidase into contact with said sample, and
  ii. measuring the change in the amount of intact substrate, a decrease in amount of this substrate being representative of endoglycosidase activity in the sample.

In this method, the substrate is directly or indirectly labeled with a first donor compound and with a second acceptor compound, and the amount of intact substrate is determined by measuring a signal emitted by the acceptor compound, this signal resulting from a transfer, via a close proximity effect, between the donor and the acceptor.

This method can be used to measure endoglycosidases capable of cleaving heparan sulfates, such as, for example, heparanase or heparitinase.

In a particular implementation of this method, the first donor compound and the second acceptor compound are fluorescent compounds, the close proximity transfer is an energy transfer and the signal emitted is a fluorescent signal.

The term "direct labeling" is intended to mean attachment of the fluorescent label to a functional group present on, or previously introduced onto, or generated on the substrate. A spacer arm can be introduced between the fluorescent label and the substrate.

The term "indirect labeling" is intended to mean attachment of the fluorescent label to the substrate via a ligand/receptor pair. In this case, the fluorescent label and the substrate are each labeled with a member of a ligand/receptor pair.

The donor fluorescent compound is a fluorescent compound which, after excitation at a given wavelength, will emit a fluorescent signal which, by performing an energy transfer, will excite the acceptor fluorescent compound. Many donor fluorescent compounds can be used in the context of the present invention. By way of example, mention may be made of the rare earth cryptates (europium, terbium) described in patents EP 180 492, EP 321 353 and EP 601 113, and also rare earth chelates.

The acceptor fluorescent compound is a fluorescent compound, which, after excitation by energy transfer from the donor compound, will emit a fluorescent signal at a given wavelength.

Many acceptor compounds exist which can be used to implement the methods according to the present invention, among which are: allophycocyanins, crosslinked allophycocyanins such as XL665 (CIS Bio International), cyanins such as Cy5, rhodamines, squaraines, bodipy dyes and fluoresceins.

Those skilled in the art are able to select the appropriate acceptor fluorescent compound as a function of the donor fluorescent compound chosen.

The method for determining endoglycosidase enzyme activity described above may make it possible to study the effects of modulation of this enzyme activity, exerted by compounds the testing of which is desired.

The expression "modulation of enzyme activity" is intended to mean inhibition or activation of this enzyme activity, regardless of the mechanism.

The invention therefore also relates to a method for detecting a compound capable of modulating enzyme activity of the endoglycosidase type, comprising the following steps:

i. bringing a substrate which can be cleaved by an endoglycosidase into contact with an endoglycosidase, in the presence or absence of the test compound,
  ii. measuring the change in the amount of intact substrate, and
  iii. comparing the change in the amount of substrate measured in the absence of the test product with that measured in the presence of the test product.

In this method, the substrate is directly or indirectly labeled with a first donor compound and with a second acceptor compound, and the amount of intact substrate is determined by measuring a signal emitted by the acceptor compound, this signal resulting from a transfer via a close proximity effect between the donor and the acceptor.

In the latter method, the endoglycosidase used can in particular be a heparanase chosen from recombinant heparanase, purified heparanase, nonpurified heparanase and heparitinase.

In a particular implementation of this method, the first donor compound and the second acceptor compound are fluorescent compounds, the close proximity transfer is an energy transfer and the signal emitted is a fluorescent signal.

The substrate used in the preceding methods can be chosen from heparan sulfate proteoglycans (HSPG) and their derivatives, extracellular matrix-associated heparan sulfates (HSs) and their derivatives, heparin, and heparan sulfates (HSs) or their derivatives, and will contain at least one unit of formula below:

in which,
  $R_1$ and $R_3$ are chosen from the groups: H, $SO_3H$, $SO_3H$,
  $R_2$ is chosen from the groups $SO_3H$, $SO_3H$—, $C(O)CH_3$,
  $X_1$ and $X_2$ represent H, COOH, COO—.

The substrate derivatives are HSs or HSPGs which have undergone minor modifications which do not disturb the enzyme-substrate recognition. More precisely, these substrate derivatives can be cleaved by an enzyme having activity of the heparanase type.

Figure 1:
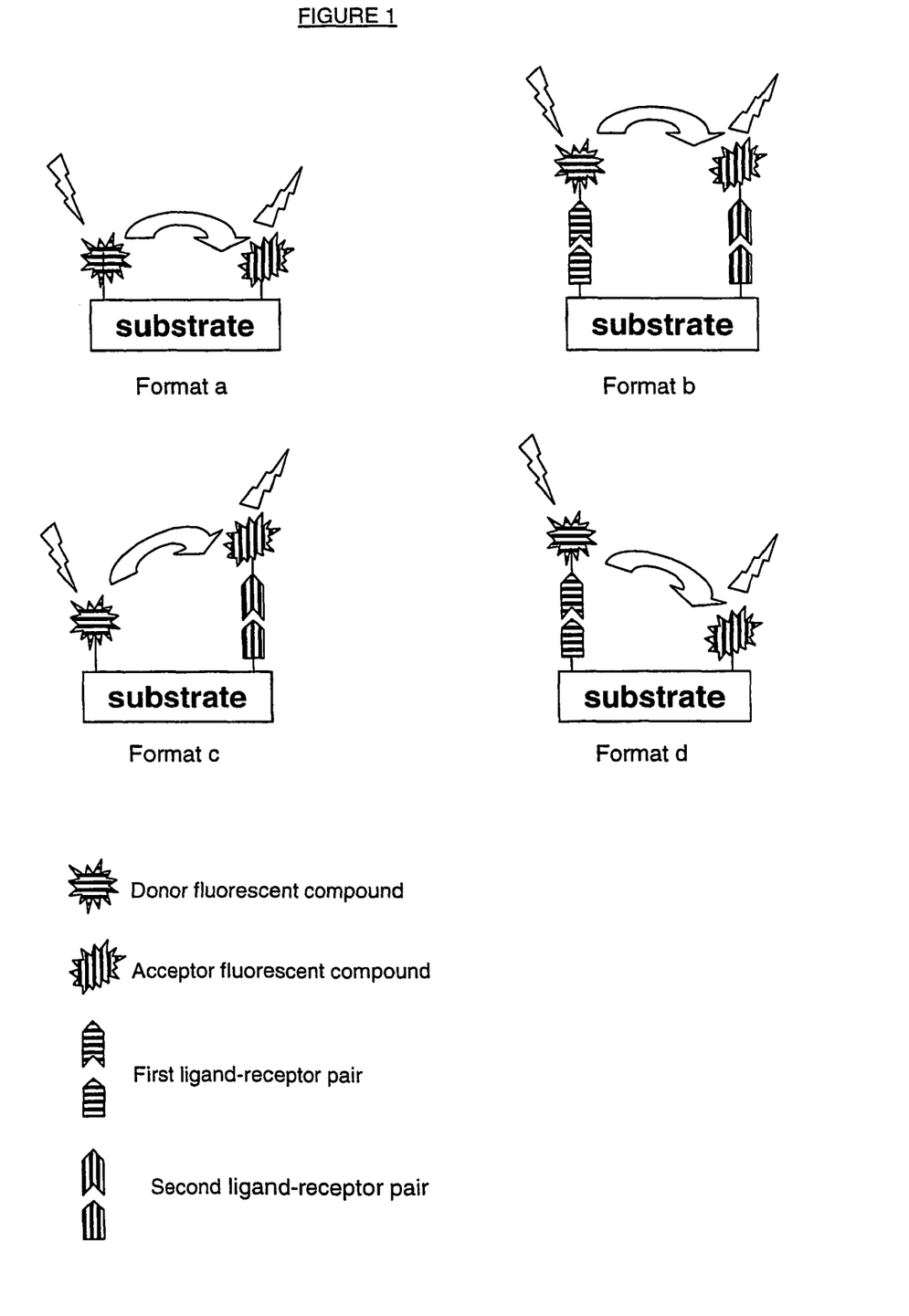
FIG. 1 illustrates representative assay formats which can be used for implementing the methods of the instant invention In format (a) the substrate is covalently attached to a donor fluorescent compound and to an acceptor fluorescent compound.

The methods according to the invention can be implemented using various formats. The following formats are the preferred formats and are represented in FIG. 1.

Format a: the substrate can be covalently attached to a donor fluorescent compound and to an acceptor fluorescent compound.

Format b: the substrate is covalently attached to a member of a first ligand-receptor pair and to a member of a second ligand-receptor pair, the donor fluorescent compound is covalently attached to the other member of the first ligand-receptor pair and the donor fluorescent compound is attached to the other member of the second ligand-receptor pair.

Format c: the substrate is covalently attached to the donor fluorescent compound and is covalently attached to a member of a ligand-receptor pair, and the acceptor fluorescent compound is covalently attached to the other member of said ligand-receptor pair.

Format d: the substrate is covalently attached to the acceptor fluorescent compound and is covalently attached to a member of a ligand-receptor pair, and the donor fluorescent compound is covalently attached to the other member of said ligand-receptor pair.

The "ligand-receptor pair" denotes two binding partners such as the pairs: hapten/antibody; DNP/anti-DNP antibody, in which DNP represents dinitrophenol; GST/anti-GST antibody, in which GST represents glutathione S-transferase; biotin/avidin; 6HIS/anti-6HIS antibody, in which 6HIS is a peptide consisting of 6 histidines; Cmyc/anti-Cmyc antibody, in which Cmyc is a peptide consisting of amino acids 410-419 of the human Cmyc protein; FLAG/anti-FLAG® antibody, in which FLAG is a peptide of 4 amino acids; or HA/anti-HA antibody, in which HA is an influenza hemagglutinin epitope consisting of 9 amino acids. Other pairs can be used.

These "tag/antitag" systems are well known to those skilled in the art and are commercially available.

The donor fluorescent compound, the acceptor fluorescent compound and the members of the first and second ligand-receptor pairs can be covalently attached to the substrate using reactional groups such as maleimide, carboxylic acid, haloacetamide, alkyl halide, azido, hydrazido, aldehyde, ketone, amino, sulfhydryl, isothiocyanate, isocyanate, monochlorotriazine, dichlorotriazine, aziridine, sulfonyl halide, acid halide, hydroxysuccinimide ester, hydroxysulfo-succinimide ester, imido ester, hydrazide, azidonitrophenyl, azidophenyl, azide, 3-(2-pyridyl-dithio)proprionamide, or glyoxal groups, and more particularly the groups of formula:

where n ranges from 0 to 8 and p is equal to 0 or 1, and Ar is a heterocycle with 5 or 6 ring-members comprising 1 to 3 hetero atoms, optionally substituted with a halogen atom.

These reactional groups are introduced onto the donor or acceptor fluorescent compound or onto the member of ligand-receptor pair and onto the substrate using $NH_2$, COOH, and/or CHO functions present on these molecules.

If the substrate used is an HS, it is possible to couple the fluorescent compounds or members of ligand-receptor pairs via the amine or carboxyl functions of the HS. The use of these groups for producing conjugates is covered in "Bioconjugate Techniques", G. T. Hermanson, Academic Press, 1996.

The amine functions can be used to attach the first or the second fluorophore, or else a member of a ligand-receptor pair. To this effect, the fluorescent compounds or the members of ligand-receptor pairs are coupled with reactional groups allowing coupling with an amine of the HS or of the HSPG. By way of nonlimiting example, the first or second fluorophore, and also one of the ligand/receptor pair members, can be coupled to an isothiocyanate, isocyanate, N-hydroxysuccinimide ester, acyl azide, sulfonyl chloride, aldehyde, glyoxal, epoxide, epoxirane, carbonate, aryl halide, imido ester, carbodiimide or anhydride group.

If the carboxyl functions of the HS are used, the fluorescent compounds or ligand-receptor pair members can be coupled to groups which react with these carboxyl functions, such as diazoalkanes, diazoacetyls, carbonyldiimidazoles or carbodiimides.

If the substrate used is an HSPG, it is possible to couple the fluorescent compounds or ligand-receptor pair members via the CHO functions (after oxidation of the OH functions) of the sugars of the carbohydrate component (HS) or the amine functions of the protein component (proteoglycan).

In the methods according to the invention, the donor compound is a rare earth cryptate or chelate, and the donor fluorescent compound is chosen from rhodamines, cyanins, squaraines, bodipy dyes, fluoresceins, allophycocyanin and their derivatives. The acceptor fluorescent compound derivatives are fluorescent molecules whose spectroscopic properties are compatible with the energy transfer.

The rare earth cryptates preferentially used in the methods according to the invention are Europium cryptates of formula:

The method for detecting a compound capable of modulating enzyme activity of the heparinase type makes it possible to screen libraries of products which can in particular be anti-heparinase antibodies, natural products, synthetic products, products from a library of compounds obtained by combinatorial chemistry, peptides and proteins.

The substrates which can be used by methods consist of HS comprising biotin and DNP groups, characterized in that the DNP/HS final molar ratio is between 0.3 and 2, and is preferably equal to 0.7, and in that the biotin/HS final molar ratio is between 0.5 and 2, and is preferably equal to 1.

Other substrates which can be used by methods consist of HSPG comprising biotin and DNP groups, characterized in that the DNP/HSPG final molar ratio is between 6 and 15, and is preferably equal to 10.8, and in that the biotin/HSPG final molar ratio is between 6 and 15, and is preferably equal to 8.

Finally, the invention also relates to a kit containing the reagents required to carry out the methods according to the invention, and in particular the following elements:
- a substrate which can be cleaved by an enzyme having activity of the heparanase type,
- a donor fluorescent compound covalently attached or capable of indirectly attaching to said substrate,
- an acceptor compound covalently attached or capable of indirectly attaching to said substrate, said elements possibly being in the same bottle or in different bottles when the fluorescent compounds are not covalently attached to said substrate.

The kit according to the invention preferably contains:
- a heparan sulfate labeled with biotin and with DNP
- a rare earth cryptate coupled to an anti-DNP antibody
- XL665 coupled to streptavidin.

Another kit according to the invention contains:
- a heparan sulfate proteoglycan labeled with biotin and with DNP
- a rare earth cryptate coupled to an anti-DNP antibody
- XL665 coupled to streptavidin.

The methods according to the invention have many advantages compared to the methods of the prior art, and in particular:
- they are very simple to carry out since it is sufficient to bring the various reagents into contact in order to be able to obtain a fluorescent signal characteristic of enzyme activity of the heparanase type. No chemical treatment or separation step is necessary.
- The volumes used are very small (20 µl per well), which allows the assay to be miniaturized, and makes it possible to save on reagents. Less than 30 ng of substrate is used in example 4, whereas in application WO 00/03036, for example, from 5 to 50 µg of substrate are used. The same is true for the amount of enzyme used in the assay. Greater minaturization can be envisioned and is simple to implement with a suitable reader.
- The incubation times for the reagents are short: as is shown in example 4, one hour of incubation is sufficient after the enzyme reaction in order to obtain a signal. The methods according to the invention therefore make it possible to rapidly screen libraries of molecules capable of modulating heparanase activity.

The following examples illustrate in a nonlimiting manner the preferred implementations of the methods according to the invention:

BRIEF DESCRIPTION OF THE DRAWINGS

In format (b) the substrate is covalently attached to a member of a first ligandreceptor pair and to a member of a second ligand-receptor pair, the donor fluorescent compound is covalently attached to the other member of the first ligand-receptor pair and the donor fluorescent compound is attached to the other member of the second ligandreceptor pair.

In format (c) the substrate is covalently attached to the donor fluorescent compound and is covalently attached to a member of a ligand-receptor pair, and the acceptor fluorescent compound is covalently attached to the other member of said ligandreceptor pair.

In format (d) the substrate is covalently attached to the acceptor fluorescent compound and is covalently attached to a member of a ligand-receptor pair, and the donor fluorescent compound is covalently attached to the other member of said ligandreceptor pair.

EXPERIMENTAL SECTION

The following abbreviations are used:
DNP: dinitrophenol
EDC: 1-ethyl-3-(3-dimethylaminopropyl)carbodiimide
HS: heparan sulfate
NHS: N-hydroxysuccinimide A/ Use of a Substrate of the Heparan Sulfate Type
In this case, the substrate is functionalized using the COOH and $NH_2$ functions of the HS.

Example 1

Preparation of a DNP-HS-Biotin Substrate

Reagents Used:
Solution of HS at 20 mg/ml: 10 mg HS+0.5 ml 10 mM $PO_4$(Na/K) buffer, pH 7.0, 0.15M NaCl.
Solution of EDC at 20 mM: 2.4 mg EDC (PIERCE)+0.625 ml 0.1 M MES buffer, pH 6.0.
47 mM 5-(biotinamide)pentylamine solution: 4.2 mg 5-(biotinamide) pentylamine (PIERCE)+0.271 ml 0.1 M MES buffer, pH 6.0.
Solution of DNP-NHS at 1 mg/ml: 3 mg DNP-NHS (CIS-Bio)+1.0 ml DMSO (Sigma D8418).

Biotin Labeling
0.25 ml of a solution of HS at 20 mg/ml (Seikagaku) are mixed with 0.125 ml of 47 mM 5-(biotinamide)pentylamine solution. The mixture is incubated for 18 h at room temperature in the presence of 0.125 ml of a 20 mM EDC solution. The reaction is then stopped by adding 1.5 ml of $PO_4$(Na/K) buffer (10 mM) containing NaCl (0.15M), pH 7. The mixture is then dialyzed for 1.5 h, using a Slide-A-Lyzer dialysis system (Pierce), against 600 ml of 0.1M $PO_4$(Na/K) buffer, pH 7. Two further dialyses carried out for 3 h in 600 ml of 10 mM $PO_4$(Na/K) buffer, pH 7, and for 16 h against 600 ml of 50 nM borate buffer, pH 8.3, make it possible to obtain 2 ml of solution containing the biotinylated HS, hereinafter referred to as biotin-HS.

DNP Labeling
The 2 ml solution of biotin-HS is mixed with 1 ml of a solution of DNP-NHS at 3 mg/ml and incubated at room temperature in the presence of 1 ml of 50 mM borate buffer, pH 8.3, and 0.5 ml of DMSO for 2 h. The reaction mixture is then separated by chromatography on a column of the Sephadex G25 SF type (Pharmacia), eluted with a 0.1M $PO_4$(Na/K) buffer, pH 7. An 8.83 ml solution of heparan sulfate labeled with biotin and DNP, hereinafter referred to as "DNP-HS-biotin", is thus obtained.

Example 2

Determination of the Final Molar Ratios

Assaying of the DNP-HS-Biotin:
A kit for assaying HSs (Byscan, Biocolor Ltd) makes it possible to determine the concentration of DNP-HS-biotin.

Assaying of the DNP:
The DNP concentration is determined by measuring the absorbance of a solution of DNP-HS-biotin at 360 nm on a spectrophotometer; the DNP concentration is determined by comparing the measured value with a standard curve.

Assaying the Biotin:
The biotin concentration is measured using an assay based on the FRET phenomenon: a first curve is established by bringing into contact known concentrations of biotin, a cryptate-streptavidin donor conjugate and an XL-biotin acceptor conjugate, and measuring the signal obtained on a Rubystar fluorimeter (BMG). A displacement curve is plotted and will be used as a standard range.

The same experiment is carried out, replacing the biotin with the DNP-HS-biotin to be assayed. The value of the signal obtained is referred to the standard range, which makes it possible to determine the biotin concentration.

The Rmf values obtained are: DNP/HS=0.7 and biotin/HS=1

Example 3

Assaying the DNP-HS-Biotin Compound Using a Homogeneous Time-Resolved Fluorescence (HTRF®) Measurement Method The present example makes it possible to validate the use of the DNP-HS-biotin product in an assay based on the time-resolved measurement of fluorescence emitted by radiative transfer, in homogeneous medium.

Reagents Used:
Streptavidin-XL conjugate, solution at 10 µg/ml: 3.2 µl of SA-XL (CIS bio international) at 625 µg/ml+197 µl of 0.1M $PO_4$(Na/K) buffer, pH7.0; 0.1% BSA 0.4M KF.
Streptavidin-XL conjugate, solution at 1 µg/ml: 18 µl of SA-XL (CIS bio international) at 20 g/ml+162 µl of 0.1M $PO_4$(Na/K) buffer, pH7.0; 0.1% BSA 0.4M KF.
Anti-DNP antibody-cryptate conjugate (hereinafter referred to as aDNP-K), solution at 1 µg/ml: 4.5 µl of aDNP-K (CIS bio international) at 100 µg/ml+445 µl of 0.1M $PO_4$(Na/K) buffer, pH 7.0, 0.1% BSA 0.4M KF.
DNP-HS-biotin solutions of varying concentration (from 22.2 to 5 400 ng/ml) are prepared from the solution obtained in example 1, in a 0.1 M $PO_4$(Na/K) buffer, pH 7.

The assay is carried out on multiwell microplates. Each well contains 5 µl of aDNP-K (1 µg/ml), 5 µl of SA-XL (1 µg/ml or 10 µg/ml) and 10 µl of DNP-HS-biotin of varying concentration. The plates are analyzed on a Rubystar spectrofluorimeter (BMG) after incubation for 1 h at ambient temperature (excitation 337 nm, emission 620 and 665 nm).

Figure 2:
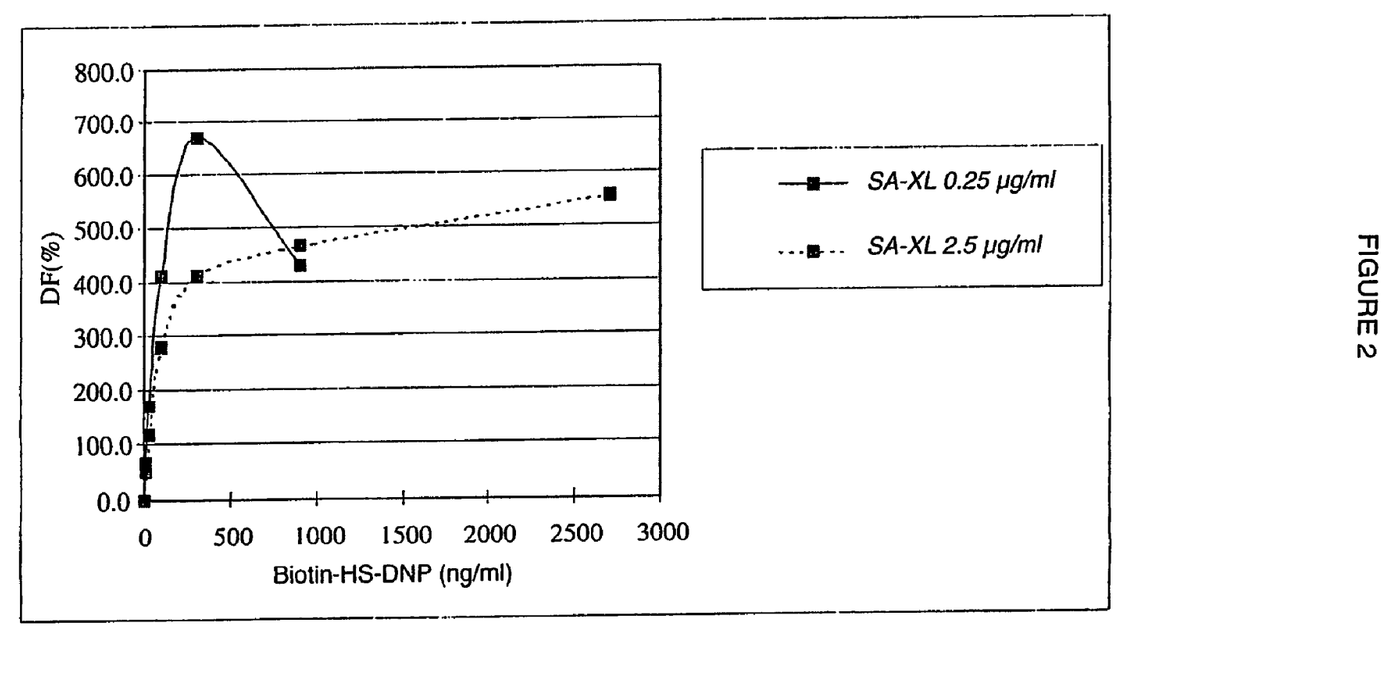
FIG. 2 shows the change in the signal as a function of the concentration of DNRHS-biotin.

The results obtained are expressed in FIG. 2, which shows the change in the signal as a function of the concentration of DNP-HS-biotin.

FIG. 2 shows that, surprisingly, a signal is obtained with the DNP-HS-biotin substrate, which means that an energy transfer clearly takes place between the donor compound (aDNP- K) and the acceptor compound (SA-XL). The same type of experiment carried out using other compounds (SA-K and anti-HS antibody-XL, to assay a biotin-HS substrate) did not enable a signal to be obtained, which indicated that the energy transfer could not take place in this precise case. The signal obtained using the present format correlates perfectly with the concentration of DNP-HS-biotin, which makes it possible to envision using these products to measure enzyme activity of the heparanase type.

Example 4

Assaying Activity of the Heparanase Type

Reagents Used:

Solution of heparitinase III (Sigma), from 0.2 to 20 000 µunits/ml, in 20 mM $PO_4$ buffer, pH 7.2; 0.15M NaCl; 0.1% BSA.

SA-XL solution at 1 µg/ml: 1 µl of SA-XL at 625 µg/ml (CIS bio international)+624 µl of 0.1M $PO_4$ buffer, pH 7.2; 0.4M KF NaCl; 0.1% BSA.

Solution of aDNP-K at 0.8 µg/ml: 2 µl of aDNP-K at 100 µg/ml (CIS bio international)+248 µl of 0.1M $PO_4$ buffer, pH 7.2; 0.4M KF NaCl; 0.1% BSA.

Solution of DNP-HS-biotin at 1.2 µg/ml: 3.8 µl of DNP-HS-biotin at 45 µg/ml+140 µl of 20 mM $PO_4$ buffer, pH 7.2; 0.15M NaCl; 0.1% BSA.

The enzyme reaction is carried out by mixing 20 µl of DNP-HS-biotin at 1.2 µg/ml with 20 µl of heparitinase solution at varying concentration (from 0.2 to 20 000 µunits/ml).

This mixture is left at room temperature for 5 h.

10 µl of each reaction mixture are placed in microplate wells, to which 5 µl/well of aDNP-K (0.8 µg/ml) and 5 µl of SA-XL (1 µg/ml) are added.

The plate is read after one hour of incubation at room temperature, on a Rubystar spectrofluorimeter (BMG).

Figure 3:
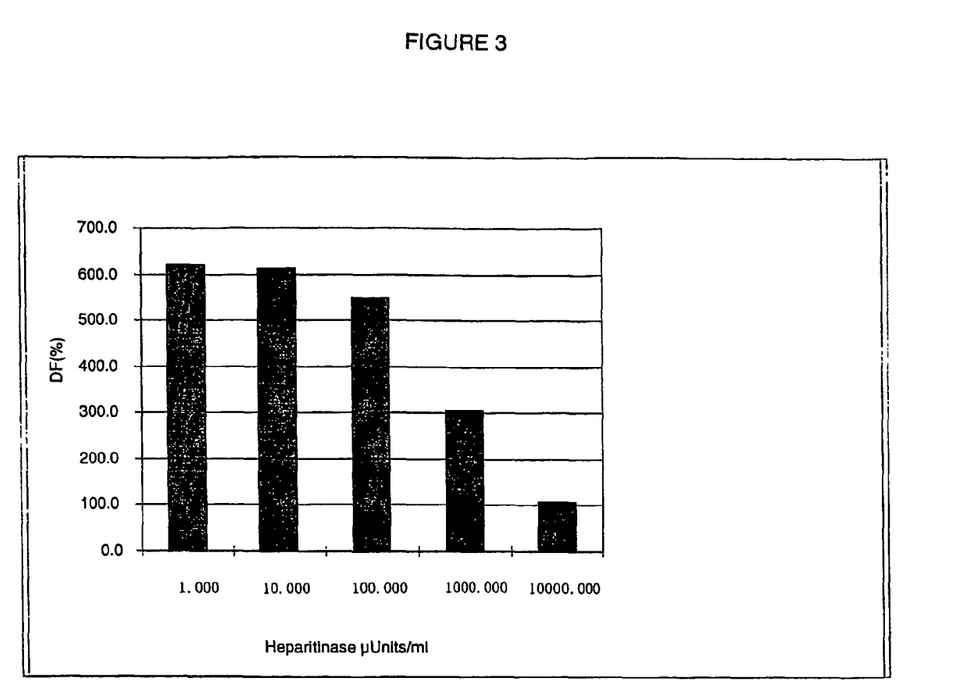
FIG. 3 shows the change in the signal for an increase in concentration of enzyme.

The results obtained are expressed in FIG. 3, which shows the change in the signal for an increase in concentration of enzyme.

The decrease in the signal correlates perfectly with the increase in the enzyme activity, i.e. the cleavage of the DNP-HS-biotin substrate. The format used is therefore entirely suitable for a method for assaying an enzyme of the heparanase type, such as heparitinase, but also for determining a modulator of this enzyme activity.

Example 5

Determination of a Modulator of Enzyme Activity of the Heparanase Type

The same procedure as in example 4 is carried out, but the various reaction mixtures are incubated with identical enzyme activities, in the presence or absence of a test product.

The percentage inhibition or activation of the enzyme due to the test compound is determined, by comparison of the results obtained in the presence and in the absence of the test product.

B/ Use of a Substrate of the Heparan Sulfate Proteoglycan (HSPG) Type

In this case, the substrate is functionalized using the OH functions of the HS and the $NH_2$ functions of the protein component (proteoglycan).

Example 6

Synthesis of the DNP-Heparan Sulfate Proteoglycan-Biotin Substrate (Hereinafter Referred to as DNP-HSPG-Biotin)

Reagents Used:
HSPG: Sigma, MW 200 kDa
Biotin hydrazide: Pierce, MW 258.33 Da
$NaIO_4$: Sigma
$NaCNBH_4$: Sigma The HSPG is dialyzed against a 100 mM carbonate solution, pH 9.

DNP Labeling

A solution of HSPG and DNP-NHS is reacted for 1 h at ambient temperature. The amounts used are such that the initial molar ratio is 15 DNPs per HSPG. The reaction mixture is then purified on a Sephadex G-25 column (NAP-5, Pharmacia) eluted with 100 mM $PO_4$ buffer, pH 7. A solution of DNP-HSPG is obtained.

Biotin Labeling

The DNP-HSPG solution obtained above is oxidized with a 10 mM $NaIO_4$ solution for 30 min at ambient temperature. After purification on a Sephadex G25 column eluted with 100 mM P buffer, pH 7.0, the oxidized DNP-HSPG solution is mixed with a solution of biotin hydrazide. The amounts used are such that the initial molar ratio is 10 biotin hydrazides per DNP-HSPG. The reaction mixture is incubated at 4° C. for 16 h and is then reduced with a 15 mM $NaCNBH_4$ solution for 40 min at 4° C. After purification on a Sephadex G215 column eluted with 100 mM $PO_4$ buffer, pH 7.0, a solution of DNP-HSPG-biotin is obtained.

Example 7

Assaying the DNP-HSPG-Biotin Compound Using a Homogeneous Time-Resolved Fluorescence (HTRF®) Measurement Method The present example makes it possible to validate the use of the DNP-HSPG-biotin product in an assay based on the time-resolved measurement of fluorescence emitted by radiative transfer, in a homogeneous medium.

Reagents Used:

Streptavidin-XL conjugate (hereinafter referred to as Sa-XL), solution at 10 µg/ml prepared from Sa-XL at 625 µg/ml (CIS bio international) diluted in a 0.1M $PO_4$(Na/K) buffer, pH 7.0; 0.2% BSA 0.8M KF.

Anti-DNP antibody-cryptate conjugate (hereinafter referred to as aDNP-K), solution at 0.4 µg/ml prepared from aDNP-K at 100 µg/ml (CIS bio international) diluted in 0.1M $PO_4$(Na/K) buffer, pH 7.0, 0.2% BSA 0.8M KF.

Streptavidin-cryptate conjugate (hereiniafter referred to a Sa-K), solution at 0.8 µg/ml prepared from Sa-K at 200 µg/ml (CIS bio international) diluted in a 0.1M $PO_4$(Na/K) buffer, pH 7.0; 0.2% BSA 0.8M KF.

Anti-DNP antibody-XL conjugate (hereinafter referred to as aDNP-XL), solution at 4 µg/ml prepared from aDNP-XL at 250 µg/ml (CIS bio international) diluted in a 0.1M $PO_4$(Na/K) buffer, pH 7.0; 0.2% BSA 0.8M KF.

DNP-HSPG-biotin solutions at varying concentration (from 10 to 5 000 ng/ml) are prepared from the solution obtained in example 6, in a 0.1M $PO_4$(Na/K) buffer, pH 7.

The assay is carried out on multiwell microplates. Each well contains 100 μl of DNP-HSPG-biotin at varying concentration, 50 μl of Sa-XL and 50 μl of aDNP-K. or 100 μl of DNP-HSPG-biotin at varying concentration, 50 μl of Sa-K and 50 μl of aDNP-XL. The plates are analyzed on a Rubystar spectrofluorimeter (BMG) after incubation for 1 h at room temperature (excitation 337 nm, emission 620 and 665 nm).

Figure 4:
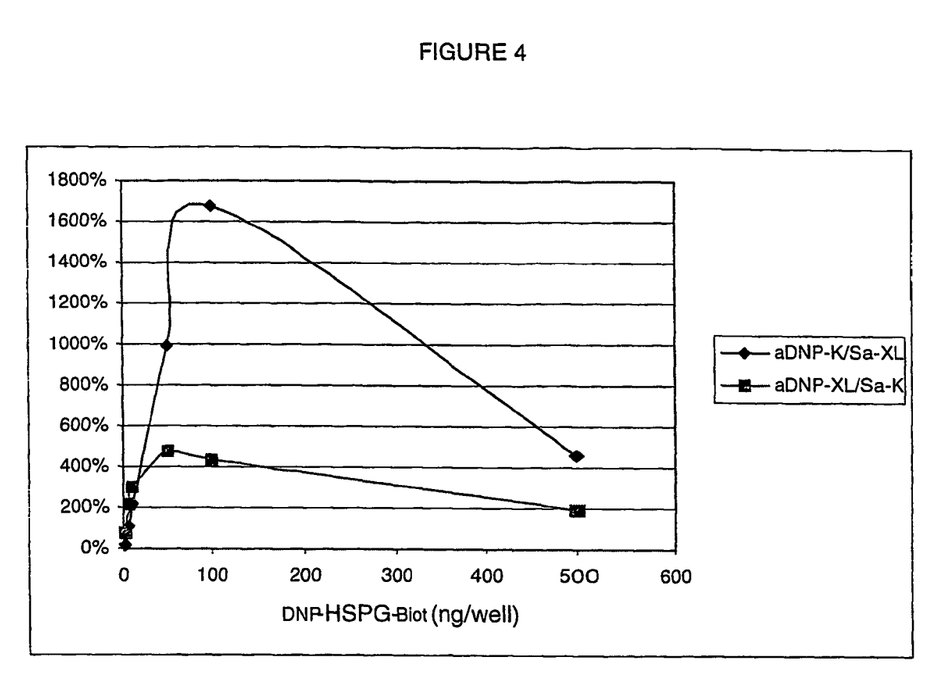
FIG. 4 shows the change in the signal as a function of the concentration of DNP-HSPG-biotin.

The results obtained are expressed in FIG. 4, which shows the change in the signal as a function of the concentration of DNP-HSPG-biotin.

FIG. 4 shows that a signal is obtained with the DNP-HSPG-biotin substrate, which means that an energy transfer clearly takes place between the donor compound (aDNP-K or Sa-K) and the acceptor compound (SA-XL or aDNP-XL). The signals obtained using these formats correlate perfectly with the concentration of DNP-HS-biotin, which makes it possible to envision using these products to measure enzyme activity of the heparanase type.

We claim:

1. A method for determining endoglycosidase enzyme activity in a sample, comprising:
   i. bringing a substrate which can be cleaved by said endoglycosidase into contact with said sample, and
   ii. measuring a change in the amount of intact substrate,
      a decrease in the amount of this substrate being representative of endoglycosidase activity in the sample,
   wherein the substrate is directly or indirectly labeled with a first donor compound and with a second acceptor compound, and the amount of intact substrate is determined by measuring a signal emitted by the acceptor compound, this signal resulting from a transfer, via a close proximity effect, between the donor and the acceptor.

2. The method as claimed in claim 1, wherein the first donor compound and the second acceptor compound are fluorescent compounds, the close proximity transfer is an energy transfer, and the signal emitted is a fluorescent signal.

3. The method as claimed in claim 1, wherein the endoglycosidase is an enzyme of the heparanase type which is recombinant heparanase, purified heparanase, nonpurified heparanase or heparitinase.

4. The method as claimed in claim 1, wherein the substrate is a heparan sulfate proteoglycan or a derivative thereof, extracellular matrix-associated heparan sulfate or a derivative thereof, heparin, or heparan sulfate or a derivative thereof, containing from 1 to 30 units of formula:

wherein
$R_1$ and $R_3$ are, independently of one another, H, $SO_3H$, or $SO_3H-$,
$R_2$ is $SO_3H$, $SO_3H-$, or $C(O)CH_3$, and
$X_1$ and $X_2$ are, independently of one another, H or COOH.

5. The method as claimed in claim 4, wherein the substrate is covalently attached to a donor fluorescent compound and to an acceptor fluorescent compound.

6. The method as claimed in claim 4, wherein the substrate is covalently attached to a member of a first ligand-receptor pair and to a member of a second ligand-receptor pair, and wherein the donor fluorescent compound is covalently attached to the other member of the first ligand-receptor pair and the donor fluorescent compound is attached to the other member of the second ligand-receptor pair.

7. The method as claimed in claim 4, wherein the substrate is covalently attached to the donor fluorescent compound and is covalently attached to a member of a ligand-receptor pair, and the acceptor fluorescent compound is covalently attached to the other member of said ligand-receptor pair.

8. The method as claimed in claim 4, wherein the substrate is covalently attached to the acceptor fluorescent compound and is covalently attached to a member of a ligand-receptor pair, and the donor fluorescent compound is covalently attached to the other member of said ligand-receptor pair.

9. The method as claimed in claim 6, wherein the first and the second ligand-receptor pair are different and are chosen from the pairs: hapten/antibody, DNP/anti-DNP antibody, GST/anti-GST antibody, biotin/avidin, 6HIS/anti-6HIS antibody, Cmyc/anti-Cmyc antibody, FLAG/anti-FLAG antibody, or HA/anti-HA antibody.

10. The method as claimed in claim 1, wherein the donor compound is a rare earth cryptate or chelate, and the acceptor fluorescent compound is a rhodamine, cyanin, squaraine, bodipy dye, fluorescein, allophycocyanin or a derivative thereof.

* * * * *